United States Patent [19]

Parent et al.

[11] Patent Number: 5,747,672
[45] Date of Patent: May 5, 1998

[54] ULTRASONIC PROBES FOR USE IN HARSH ENVIRONMENTS

[75] Inventors: Luc Parent, Chicoutimi; Guy Peloquin, Jonquiere; Gilles Tremblay, St-Fulgence; Andre Vaillancourt, Larouche, all of Canada

[73] Assignee: Alcan International Limited, Montreal, Canada

[21] Appl. No.: 850,642

[22] Filed: May 2, 1997

Related U.S. Application Data

[63] Continuation of Ser. No. 522,019, Aug. 31, 1995, abandoned.

[51] Int. Cl.$^6$ .................................................. G01N 29/00
[52] U.S. Cl. ............... 73/61.79; 73/61.49; 73/61.75; 73/861.25; 310/340; 367/141; 367/155; 128/662.03; 128/663.01
[58] Field of Search ..................... 73/61.49, 61.75, 73/61.79, 64.42, 590, 861.25, 702; 310/340, 344; 128/662.03, 663.01; 367/141, 155

[56] References Cited

U.S. PATENT DOCUMENTS

| | | | |
|---|---|---|---|
| 3,204,458 | 9/1965 | Gillen | 73/861.26 |
| 4,196,631 | 4/1980 | Deom et al. | 73/644 |
| 4,336,808 | 6/1982 | Ohno et al. | 128/662.03 |
| 4,455,873 | 6/1984 | Abts | 73/629 |
| 4,497,208 | 2/1985 | Oja et al. | 73/584 |
| 4,509,360 | 4/1985 | Erwin et al. | 73/61.75 |
| 4,563,274 | 1/1986 | Rothon et al. | 210/101 |
| 4,616,152 | 10/1986 | Saito et al. | 310/334 |
| 4,662,212 | 5/1987 | Noguchi et al. | 73/24 |
| 4,963,782 | 10/1990 | Bui et al. | 310/358 |
| 4,969,362 | 11/1990 | Zacharias et al. | 73/597 |
| 4,984,449 | 1/1991 | Caldwell et al. | 73/49.2 |
| 5,003,516 | 3/1991 | Sato et al. | 367/150 |
| 5,050,137 | 9/1991 | Sato et al. | 367/150 |
| 5,176,140 | 1/1993 | Kami et al. | 128/662.03 |
| 5,343,443 | 8/1994 | Merewether | 367/152 |
| 5,381,795 | 1/1995 | Nordgren et al. | 128/663.01 |
| 5,423,220 | 6/1995 | Finsterwald et al. | 73/642 |
| 5,485,744 | 1/1996 | Akutagawa et al. | 73/61.49 |

OTHER PUBLICATIONS

Kay–Ray/Sensall, Sludge/Slurry Level Control System, Data Sheet, 2 Pages, 1991.
Kay–Ray/Sensall, Sludge Density Controller, Data Sheet, 2 Pages, 1991.
American Piezo Ceramics Inc., Lead Zirconate Titanate and Lead Metaniobate Ceramics, 3 pages.
Data Sheet, Rema Line 40/160°, 1 Page.
Sigradur, The Glassy Carbon From Sigri, 9 Pages.

*Primary Examiner*—Hezron E. Williams
*Assistant Examiner*—Richard A. Moller
*Attorney, Agent, or Firm*—Cooper & Dunham LLP

[57] ABSTRACT

An ultrasonic device for detecting concentrations of solids or positions of solid/liquid interfaces in liquid media, particularly Bayer process liquids. The device comprises at least one piezoelectric element provided with electrodes; electrical circuit elements connected to the electrodes for conveying electrical signals, in use, to and from control apparatus; an ultrasound-transparent window, made of glassy carbon, positioned adjacent to the or each piezoelectric element; a protective matrix, preferably of epoxy resin, embedding and surrounding said the or each piezoelectric element and the electrodes while allowing ultrasonic waves to pass through the or each adjacent window to or from the piezoelectric element, and an external protective cover, preferably comprising an elastomer that is resistant to caustic alkali and has a smooth and non-porous surface, forming an exterior of the device except at the or each window. The use of glassy carbon for the windows makes the probes resistant to corrosion and scaling without impeding the effectiveness of the device. Further improved scaling resistance is provided by an elastomeric material preferably used as the external protective cover.

9 Claims, 2 Drawing Sheets

ULTRASONIC PROBES FOR USE IN HARSH ENVIRONMENTS

This is a continuation of application Ser. No. 08/522,019 filed Aug. 31, 1995, abandoned.

BACKGROUND OF THE INVENTION

I. Field of the Invention

This invention relates to ultrasonic probes or detection devices intended for measuring concentrations of solids in harsh environments. More particularly, the invention relates to ultrasonic probes intended for use in highly corrosive and scale-forming conditions, e.g. in hot, alkaline slurries and solutions encountered in various industrial processes.

II. Description of the Prior Art

It is often necessary in industrial processes to detect the concentrations of solids suspended in liquids or to detect the vertical levels of solid/liquid interfaces so that various process steps, such as emptying or purging of process vessels, can be carried out when required. For example, in the Bayer process for the production of purified alumina, bauxite is dissolved in hot caustic soda solutions in a series of treatment tanks leaving suspended particles of so-called "red mud" and other tailings. The process must be controlled to transfer, dispose of, or treat such deposits as they are formed, or before they become excessive.

The use of ultra-sonic probes for this purpose has become popular since probes of this type are quite accurate and responsive. However, industrial processes in general, and the Bayer process in particular, present harsh operational environments for detection apparatus, causing rapid scaling and corrosion that can dramatically reduce the operational lifetimes of such probes in the service environment. For example, the conditions existing in Bayer process plants involve highly alkaline solutions of sodium aluminate liquor, whose caustic concentration (expressed as equivalent $Na_2CO_3$) is 180 g/L or higher, containing 120 g/L or higher of dissolved alumina, and containing suspended particles of red mud. These solutions are saturated in alumina, dissolved silica, and a complex compound of sodium, aluminum and silicate, known as the desilication product. The temperature of these solutions is between 60° and 105° C. Because they are supersaturated, highly alkaline and hot, they are both very corrosive to many materials of construction, and cause the formation of tightly adherent layers of scale on any surfaces with which they come in contact.

Ultra-sonic probes used in such typical Bayer process conditions usually remain operational for only one to two months at best, and sometimes for as little as one day. This has been found to be the case even when attempts have been made to protect the probes with coatings, casings or housings made of conventional protective materials, such as TEFLON (trademark) or other plastics. While such protective measures may reduce corrosion to some extent, excessive corrosion still takes place in a relatively short period of time and the deposition of scale (which can attenuate or eliminate the ultrasonic signal) still remains a major problem.

Various attempts have been made in the past to protect ultrasonic devices from harsh environments of various kinds. For example, in U.S. Pat. No. 4,662,212 issued May 5, 1987, Noguchi et al. disclose an ultrasonic gas concentration measuring instrument that is made dampproof by utilizing a sealing material selected from silicone resin, epoxy resin and polyurethane and depositing, by vacuum evaporation or similar techniques, a thin film of non-conductive material (e.g. SiO, $SiO_2$ or a fluorine-based resin) or a conductive material (e.g. various metals) over the sealing material to protect the device against penetration by water vapor.

It has also been recognized that it is helpful to protect the piezoelectric crystals from direct exposure to the medium in which it is immersed. For example, protection has been suggested for the piezoelectric crystals or the electrodes connected thereto by layers of ceramics, glass, and coatings of resins and insulating paint (U.S. Pat. No. 5,176,140 to Kami et al.), encapsulation in epoxy resin (U.S. Pat. No. 4,984,449 to Caldwell and U.S. Pat. No. 4,616,152 to Saito et al.), coating of the electrodes with thin layers or conductive material (e.g. SiO, $SiO_2$ or a fluorine-based resin) or a conductive material (e.g. various metals) around the electrodes of the device to protect them against attack by water vapor (U.S. Pat. No. 4,662,212 to Noguchi et al.) and protection of the face of the piezoelectric crystals by covering them with a thin layer of metal produced by cathodic sputtering.

However, the devices protected by these known methods are not generally intended for use in extremely harsh industrial environments, e.g. highly alkaline or acidic conditions, and are expensive to produce and/or would not have the required service life desired for such devices in the applications intended for the present invention.

SUMMARY THE INVENTION

An object of this invention is to provide probes or measuring devices suitable for use in harsh environments encountered in industrial processes.

Another object of the invention is to provide probes or measuring devices that have good service lifetimes in highly alkaline conditions at elevated temperatures.

Another object of the invention is to provide protection for ultrasonic probes against highly alkaline or acidic conditions.

Yet another object of the invention is to provide protection for ultrasonic probes against undue scaling by solid deposits.

According to one aspect of the invention, there is provided an ultrasonic device for detecting concentrations of solids or positions of solid/liquid interfaces in liquid media, comprising: at least one piezoelectric element provided with electrodes; electrical circuit elements connected to said electrodes for conveying electrical signals, in use, to and from control apparatus; an ultrasound-transparent window, comprising glassy carbon, positioned adjacent to said at least one piezoelectric element; a protective matrix embedding and surrounding said at least one piezoelectric element and said electrodes while allowing ultrasonic waves to pass through said adjacent window to or from said at least one piezoelectric element; and an external protective cover forming an exterior of said device except at said window.

It has been found that glossy carbon is resistant to corrosion and scaling, as well as being transparent to ultrasound. The provision of ultrasonic probes with windows of such material as well as with other protective measures, keeps the devices operational for long service lives in harsh conditions.

In the devices of the invention, the external protective cover is made of, or coated externally with, an elastomer that is chemically inert in the presence of hot caustic solutions, has a very smooth surface, and less than 1% porosity, and that is non-adherent to alumina hydrate (alumina precipitated from aluminate solutions). Natural rubbers, or mixtures of predominantly natural rubbers and synthetic rubbers, are most preferred.

The devices of the invention may include those types of devices which rely on a single piezoelectric element to both generate and detect (reflected) ultrasonic waves, devices which contain two or more piezoelectric elements, one to generate the ultrasonic waves and one to detect reflected waves, and devices containing single piezoelectric elements that are provided either to generate ultrasonic waves or to detect ultrasonic waves generated by adjacent similar devices. In the latter case, two devices according to the invention are usually mounted in close spaced relationship to each other with the windows facing each other across a small gap in which the presence of solids materials can be detected.

Thus, according to another aspect of the invention, there is provided an ultrasonic device for detecting concentrations of solids or positions of solid/liquid interfaces in liquid media, comprising: a first housing having a window made of glassy carbon containing a piezoelectric element, provided with electrodes, for generating ultrasonic waves from electrical signals; a second housing having a window made of glassy carbon containing a second piezoelectric element, provided with electrodes, for detecting ultrasonic waves passing through said window; a holder for holding said first and second housings in spaced relationship with said window of said first housing facing said window of said second housing across a free space; and electrical circuit elements connected to said electrodes for conveying electrical signals, in use, to or from said first and second piezoelectric elements to control apparatus; each of said first and second housings comprising a material that is resistant to chemical attack by caustic alkali and each of said piezoelectric elements being embedded in a protective monolithic matrix within each said housing.

Devices on the invention, at least in their preferred forms, are resistant to most chemically aggressive alkaline and acidic solutions and slurries.

Most notably, ultrasonic probe devices according to the present invention have improved service lives when operated in highly alkaline solutions, e.g. Bayer process solutions, at high temperatures. For example, service lives of the devices in Bayer process plants in the conditions described above have been shown to be one year and are expected to be as long as three years, which is considerably longer than most conventional devices.

The devices can also be used with solutions encountered in other steps of the Bayer process, such precipitation crystallization and classification of the alumina from the aluminate liquor; and in other chemically aggressive applications such as in the extraction and recovery of nickel, copper, zinc, and as found in sewage treatment facilities etc.

DETAILED DESCRIPTION OF THE PREFERRED EMBODIMENTS

Figure 1:
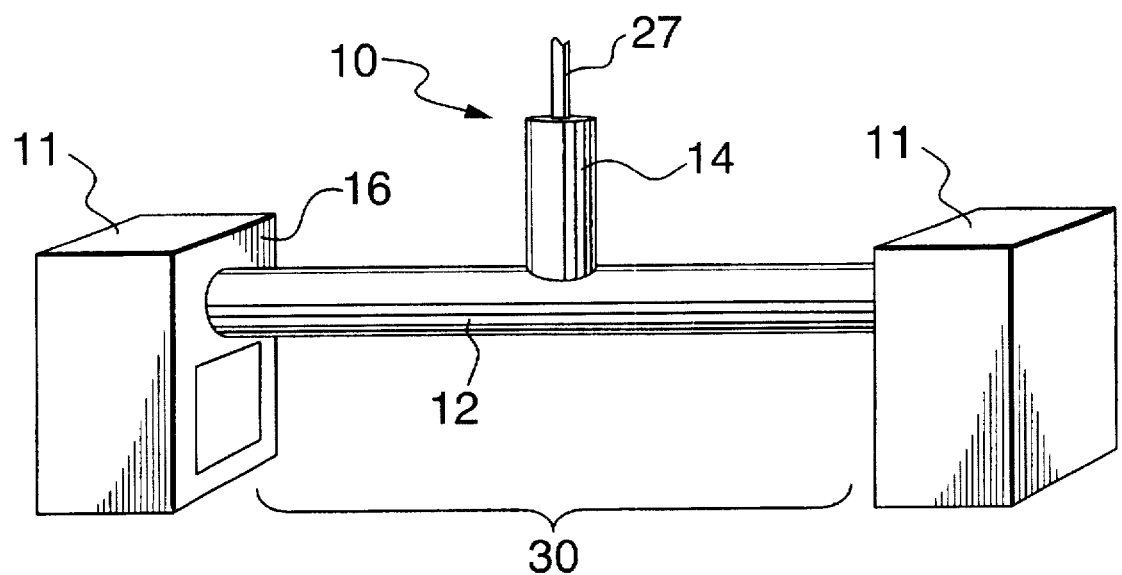
FIG. 1 is a perspective view of a probe according to one preferred aspect of the present invention.
Figure 2:
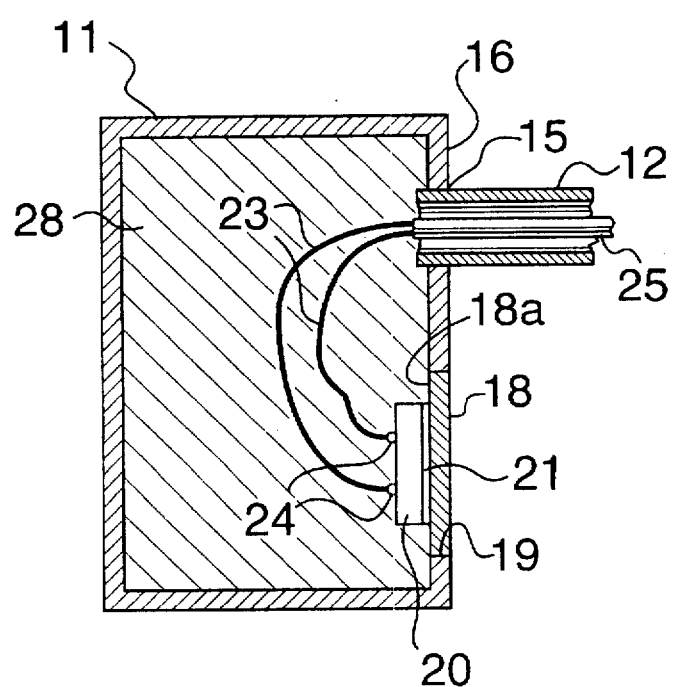
FIG. 2 is a cross-section of a housing forming part of the probe of FIG. 1.

A preferred ultrasonic probe device according to the present invention is shown in FIGS. 1 and 2. The device 10 has two rectangular housings 11 held in fixed spaced relationship by a supporting hollow steel pipe 12 that communicates with a central hollow vertical channel member 14. The steel pipe 12 acts as both a holder for the housings and as a protective conduit for electrical circuit elements. The device in this form may be immersed into a liquid for monitoring purposes.

As shown in FIG. 2, each housing 11 is formed by a hollow body provided with a hole 15 in front face 16 receiving an end of the supporting pipe 12. The housing is provided with an ultrasound-transparent window 18 sealed in a slot 19 formed in the front face 16 of the housing for transmitting and/or receiving ultrasonic waves.

A piezoelectric element 20 for generating and/or detecting ultrasonic waves is provided in the housing 11 adhered to an inner face 18a of the window 18 by a thin layer 21 of an ultrasound-transparent adhesive, e.g. epoxy resin. The piezoelectric element has electrical circuit elements 23, e.g. insulated wires, connected at electrodes 24 provided on the piezoelectric element 20. The circuit elements 23 originate from a cable 25 extending through the pipe 12 and joining with a similar cable from the other housing 11 (see FIG. 1) to form a combined cable 27 extending through channel member 14 to control apparatus (not shown). The interior of the housing 11 is completely filled with a protective monolithic matrix 28 of cured epoxy resin that embeds and surrounds the piezoelectric element 20, the electrodes 24 and at least the extreme ends of the electrical circuit elements 23 to protect these items from contact with liquid or vapors.

The housing 11 is made of, or externally coated with, a chemically inert (particularly to hot caustic alkali) elastomeric material that has a very smooth surface, a low porosity of less than 1, and a surface that is non-adherent to alumina hydrate. The elastomeric material of the housing or the external coating layer acts as an external protective cover that completely encloses the device, except at the window 18. Preferably, the elastomeric material is a natural rubber, or a mixture of predominantly (more than 50%, and generally more than 80%) natural rubber and the remainder synthetic rubber, treated to provide the indicated low porosity and high surface smoothness. The most preferred material is a product sold under the trademark REMALINE 40HR by Rematech, a division of Bremo Inc., of Chicoutimi, Quebec, Canada. This is natural rubber, black in color, that has a tensile strength (DIN 53 504) of 21 MPa, a density (DIN 53 479) of 0.99 g/cm$^2$, a tear growth resistance (DIN 53 507) of 11 N/mm, an elongation at break (DIN 53 504) of 650%, a hardness (DIN 53 506) of 40 Shore "A" ±5, a resilience (DIN 53 512) of 73% and an abrasion resistance (DIN 53 516) of 135 mm$^3$. The fact that the elastomer has a surface that is very smooth, essentially non-porous, elastomeric and resistant to attachment by alumina hydrate means that solid scale is not encouraged to become attached to the material of the housing since the solid cannot lodge in pores and since flexing of the material tends to shake the scale loose once it has formed on the surface. Additionally, elastomeric materials, especially natural rubber, are resistant to attack by strong acids and alkalis, and can form tightly sealing joints with the pipe 12 and the window 18 that prevent penetration of liquids into the interior of the housing 11.

The material used for the window 18 is glassy carbon (also known as vitreous carbon). This is a form of pure carbon embodying the properties of a ceramic material and produced by controlled pyrolysis (at temperatures, for example, of 1100°–2200° C.) of thermosetting resins, such as polyurethane or phenol-formaldehyde. A suitable material of this kind is sold under the trademarks SIGRADURK K and SIGRADURK G by Sigri Great Lakes Carbon, whose headquarters are in Wiesbaden, Germany. This material is completely non-porous, has no chemical affinity with scatle and is resistant to strong acids and alkalis. The material is, however, transparent to ultrasound, unlike the elastomeric material used for the housing 11, and thus makes an ideal material for windows 18. The thickness of the glassy carbon used for the windows 18 is preferably within the range of 1 to 4 mm. Windows as thin as 1 mm tend to be fragile and break readily upon being struck; windows thicker than 4 mm can be used, but they tend to be unduly expensive. The preferred thickness is about 4 mm, representing a reasonable compromise between cost and mechanical strength.

The complete encapsulation of the piezoelectric elements 20, electrodes 24 and connected ends of the electrical leads 23 within a monolithic matrix 28 of a protective material, preferably epoxy resin, provides good protection for these sensitive components from contact with liquids and vapors, thus minimizing corrosion. The fact that the material forms an embedding matrix, i.e. without air gaps around the piezoelectric element, is important because air gaps severely attenuate, and usually completely stop, the acoustic signals, thus making the device inoperative. The epoxy resin most preferably used for this purpose is a product sold under the trademark EB-6917 by Heresite Protective Coating, Manitowac, Wis., U.S.A. This material is particularly advantageous because it can resist attack by caustic alkali at temperatures up to 110° C. The same epoxy resin is also preferably used to as the adhesive 21 used to attach the piezoelectric element to the inner surface of the window 18.

The electrodes 24 attached to the piezoelectric elements 20 are preferably made of gold rather than the usual silver because silver is easily oxidized at temperatures around 100° C., especially by air and sulphur from the epoxy and in the elastomer. The electrical circuit elements 23 are then soldered to the gold electrodes.

The piezoelectric elements 20 themselves may be conventional ultrasonic emitter and receiver units but those sold as type APC 850 discs by American Piezo Ceramics Inc. of Mackeyville, Pa., U.S.A., are particularly preferred. These are ceramic discs made of lead zirconate titanate covered on one side with gold to facilitate making the electrical contact. The piezoelectric elements are available in different diameters. The diameter of the element determines the diameter and the focal point of the emitted beam. In the present invention, a 15 mm diameter is preferred for optimum signal strength compatible with a usable focal point. It is also preferred that the elements should be driven at a frequency of 3.75 MHz for the detection of solids in Bayer process solutions.

Referring once again to FIG. 1, it will be seen that the windows 18 of each housing 11 face each other across a free space 30, so that ultrasonic waves generated by one of the piezoelectric elements 20 in one of the housings passes through the associated window 18, traverses the free space 30, enters the window 18 of the other housing 11, and contacts the piezoelectric element 20 in that housing for detection. When the device 12 is immersed in a fluid medium, the ultrasonic waves consequently pass through the medium within the intervening free space 30.

As is well known in the art, ultrasonic waves passed through a medium in this way can be used to detect changes in density of the medium based on changes in the strength of transmission (attenuation) of the waves through the medium. The device can therefore be used to detect the presence of solids in a liquid medium or the position of a solid/liquid interface.

Figure 3:
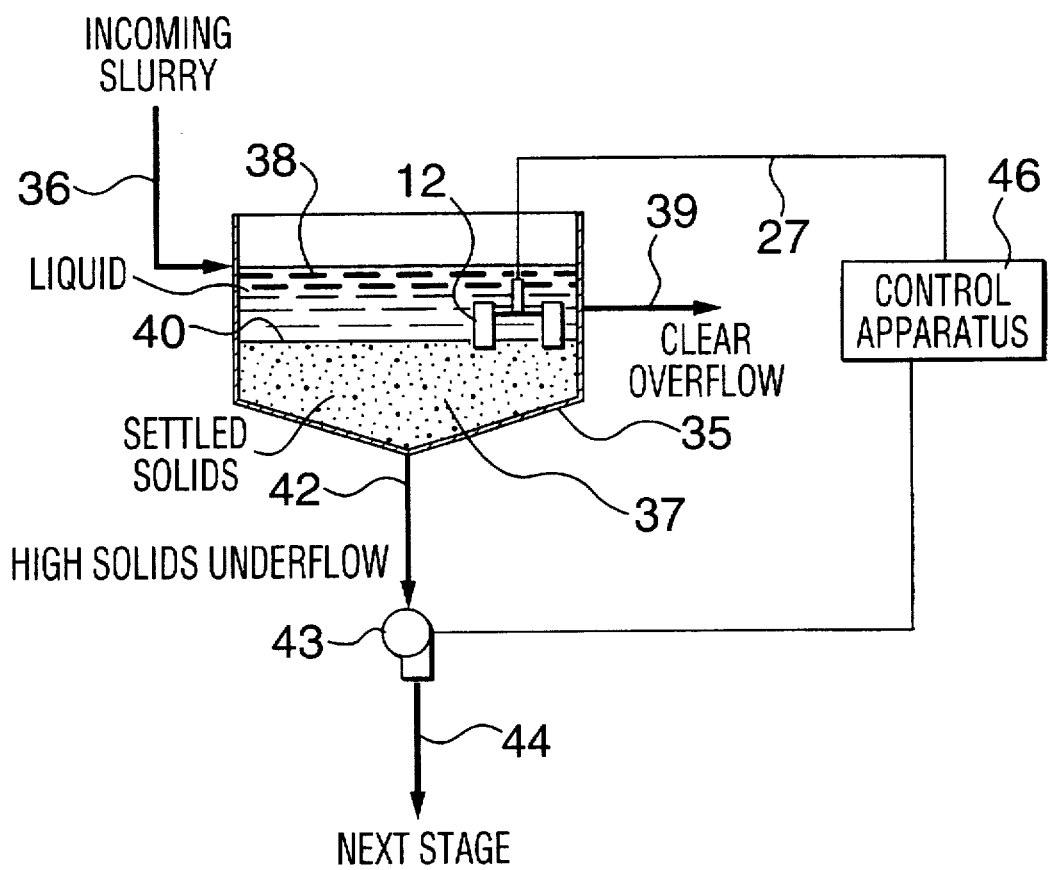
FIG. 3 is a simplified sketch showing the probe of FIGS. 1 and 2 in use in equipment used for part of the Bayer process.

FIG. 3 illustrates such an application of the device 12 of the invention. In this application, the device is immersed into a solids-containing liquid 36 introduced as incoming slurry into a gravity settler tank 35 forming part of an apparatus for carrying out the Bayer process. The solids content settles in the tank to form a settled solids layer 37 and the liquid 38 above this layer exits the tank as clear overflow 39. The interface 40 between the settled solids layer 37 and the liquid layer 38 gradually rises in the tank until the solids 37 are periodically purged through underflow outlet 42 by means of a pump 43 and passed on to the next stage of processing 44. The purge is commenced when the solid/liquid interface 40 reaches the ultrasonic device 12, which senses the presence of the solid. The detector 12 is connected by cable 27 to a control apparatus 46 that supplies electrical current to one of the piezoelectric elements 20, used as the signal generator, and monitors electrical signals from the second element, used as the signal receiver. The control apparatus 46 contains current generating and sensing electronics, and may control pump 43.

Ultrasound control apparatus suitable for use as the control apparatus 46 of the invention is well knows to persons skilled in the art and readily commercially available. For example, suitable control apparatus may be obtained from Kay-Ray/Sensall, Inc., of Mount Prospect, Ill. 60056, U.S.A., e.g. as used for SENSALL (trademark) Models 4900SL and 4940. Details of these systems are disclosed in Product Data Sheets 103-149000-12/91 of 1991 and 103-149400-12/91 also of 1991, issued by the company.

The probe 12 is preferably constricted by the following procedure. After attaching the gold electrodes 24 directly to the piezoelectric elements 20, the elements are adhered to the windows 18 via the adhesive layer 21 after sandblasting the glassy carbon of the inner surface 18a of the windows to improve the adherence of the glue to the window (adherence of all glues to glassy carbon is quite weak). The windows, with attached piezoelectric elements, are than inserted into slots 19 in the housing, the electrical circuit elements 23 are attached by soldering and the windows of the two housings 11 are aligned and held in a portable vice. Epoxy resin pre-cure is degassed under a vacuum for 30 minutes and then poured into the housings to fill about 75% of the internal volume. The assembly is cured for 10 hours at 75° C. After the first curing, the vice is removed and further epoxy resin is added to the housings. Further curing is then carried out at 75° C. for 12 hours followed by 4 hours at 120° C.

While the apparatus described above is preferred, various modifications or alterations could be made without departing from the spirit and scope of the present invention. For example, instead of providing a housing 11 made of self-supporting walls as shown, it would be possible first to create a combination of the window 18, piezoelectric element 20 and matrix 28 and then to form a layer of elastomer, or other protective covering material, over all surfaces of the combination, except for the operational part of the window 18. The thickness of the coating layer is not particularly important and, in practice, it is only necessary that the thickness be sufficient to prevent penetration of liquid into the interior of the device, for which purpose, thicknesses of 1 mm or more are preferred. When the elastomer is used to form a housing, as in the device shown in the drawings, it must be thick enough to be self-supporting, but easily cut. The elastomer sold under the trademark REMALINE is available commercially in thicknesses of 4 and 8 mm, either of which may be used.

Furthermore, devices according to the invention may be modified to make ultrasound sensors or probes of different kinds from the one already mentioned. For example, a device of the type shown in FIG. 2 could make use of a piezoelectric element 20 capable of both generating and detecting ultrasonic signals (or may incorporate two piezoelectric elements, one for generating signals and one for detecting signals), so that a second such device (as shown in FIG. 1) would not be required. Ultrasonic waves generated by the (or one of the) elements would pass through the window and, upon encountering a reflective surface (ideally a hard, dense surface, such as the wall of the vessel holding the suspension, or even the solids themselves) would be reflected back and detected by the (or a second one of the) piezoelectric element(s). The control apparatus 46 would then be modified to operate such devices. For example, for devices relying on reflection and using only a single piezoelectric element 20, a control apparatus 46 would include a timing circuit to allow the piezoelectric element to operate alternatively in the generating and detecting modes. For greater reliability and sensitivity of devices of this kind, a suitable reflective surface may be supplied as part of the equipment, e.g. an ultrasound reflector held at a fixed distance from the window 18. A suitable reflector may comprise glassy carbon imbedded in epoxy resin and covered with the same protective elastomeric material (preferably REMALINE) as the ultrasonic device. Pieces of aluminum or steel, covered with glassy carbon, may alternatively be used. The use of such reflectors would guarantee a strong reflected signal.

The invention is illustrated in more detail by the following Examples in which a probe according to a preferred form of the invention was used in three separate applications related to the Bayer Process.

EXAMPLE 1

A probe of the type shown in FIGS. 1 and 2 was tested in a high efficiency decanter, i.e. a gravity settling device used in the Bayer process for the separation of red mud residue from sodium aluminate liquor saturated in alumina. In such decanters, it is necessary to locate the position of the 30 cm wide interface between the clear supernatant liquid containing 5 g/L solids, and the zone of settling solids, containing 30 g/L solids. The liquor contained 210 g/L caustic expressed as $Na_2CO_3$ and 145 g/L of dissolved alumina, at a temperature of 108° C.

The probes of the invention operated continuously for one month without any sign of scaling or corrosion. After two months, there was a small amount of scaling on both the glassy carbon and the rubber. This was very easily removed with a plastic scraper. This is in sharp contrast to the hammer and cold chisel required to remove scale from the devices used previously. This very gentle cleaning process prolongs the expected service life to at least three years. In contrast, in the same conditions, commercially available probes required withdrawal three times per week to remove scale from the piezoelectric elements, and the probes failed after one to two months of operation.

EXAMPLE 2

A further test, using a probe as shown in FIGS. 1 and 2, was also carried out in a high efficiency decanter, in order to locate the position of the 15 cm wide interface between the zone of settling solids containing 30 g/L solids and the bed of settled solids containing 250 g/L solids. The liquor contained 210 g/L caustic expressed as $Na_2CO_3$ and 145 g/L of dissolved alumina, at a temperature of 108° C.

The probe remained fully operational and corrosion- and completely scale-free after a period of one month; thereafter, it required gentle cleaning with a plastic scraper on a monthly basis. It is expected to have a service life of at least three years.

EXAMPLE 3

This test was carried out in a red mud washing circuit, where separated red mud residues were subjected to a multiphase counter-current washing with a caustic washing solution, which was ultimately fed back to the Bayer digestion circuit. After each washing stage the resulting slurry was separate in a gravity settler into a clear overflow liquor and the solids. A probe as shown in FIG. 1 and FIG. 2 was used to determine the clarity of the overflow liquid, which was expressed as the concentration suspended solids, which ranged between 0 to 2 g/L, usually 0.20 g/L. The liquor contained 100 g/L caustic expressed as $Na_2CO_3$ and 65 g/L of dissolved alumina, at a temperature of 60° to 80° C.

The probe of the invention operated continuously for one month without any sign of scaling or corrosion. The glassy carbon windows were completely free of scale at the end of this period. Thereafter, gentle cleaning with a plastic scraper was required monthly to remove this scale. In contrast, a commercially available probe required extensive cleaning work with a cold chisel and hammer three times per week to remove scale from the piezoelectric elements, and the probe failed after 1 to 2 months of operation.

What we claim is:

1. An ultrasonic device for detecting concentrations of solids or positions of solid/liquid interfaces in corrosive and scaling liquid media, comprising: at least one piezoelectric element provided with electrodes; electrical circuit elements connected to said electrodes for conveying electrical signals, in use, to and from control apparatus; an ultrasound-transparent window made of glassy carbon, said at least one piezoelectric element being adhered to an inner surface of said window; a matrix of epoxy resin embedding and surrounding said at least one piezoelecttric element and said electrodes while allowing ultrasonic waves to pass through said window to or from said at least one piezoelectric element; and an external protective cover forming an exterior of said device except at said window, said cover comprising natural rubber or a mixture of natural and synthetic rubber, having a porosity of less than 1%.

2. A device according to claim 1 wherein said cover comprises natural rubber.

3. A device according to claim 2 wherein said natural rubber has a tensile strength of about 21 MPa, a density of about 0.99 g/cm$^2$, a tear growth resistance of about 11 N/mm, an elongation at break of about 650%, a hardness of about 40 Shore "A", a resilience of about 73% and an abrasion resistance of about 135 mm$^3$.

4. A device according to claim 1 wherein said electrodes are made of gold.

5. A device according to claim 1 wherein said window of glassy carbon has a thickness of about 1 to 4 mm.

6. An ultrasonic device for detecting concentrations of solids or positions of solid/liquid interfaces in corrosive and scaling liquid media, comprising:

a first housing having a window made of glassy carbon containing a piezoelectric element, provided with electrodes, for generating ultrasonic waves from electrical signals;

a second housing having a window made of glassy carbon containing a second piezoelectric element, provided with electrodes, for detecting ultrasonic waves passing through said window;

a holder for holding said first and second housings in spaced relationship with said window of said first housing facings said window of said second housing across a free space; and electrical circuit elements connected to said electrodes for conveying electrical signals, in use, to or from said first and second piezoelectric elements to control apparatus;

each of said first and second housings comprising natural rubber or a mixture of natural and synthetic rubber, said rubber having a porosity of less than 1% and each of said piezoelectric elements being adhered to an inner surface of said window of each said housing and being otherwise embedded in and surrounded by a monolithic matrix of epoxy resin within each said housing.

7. A device according to claim 6 wherein the first and second housings are natural rubber.

8. A device according to claim 7 wherein said natural rubber has a tensile strength of about 21 MPa, a density of about 0.99 g/cm$^2$, a tear growth resistance of about 11N/mm, an elongation at break of about 650%, a hardness of about 40 Shore "A", a resilience of about 73% and an abrasion resistance of about 135 mm$^3$.

9. A device according to claim 6 wherein said electrodes are made of gold.

* * * * *